United States Patent
Skladnev et al.

(10) Patent No.: US 6,845,264 B1
(45) Date of Patent: Jan. 18, 2005

(54) APPARATUS FOR RECOGNIZING TISSUE TYPES

(76) Inventors: Victor Skladnev, 1 Russell Street, Vaucluse, NSW 2030 (AU); Richard L. Thompson, 5 Yeats Avenue, Killarney Heights, NSW 2087 (AU); Andrew R. Bath, 19/169 Walker Street, Quakers Hill, NSW 2763 (AU)

( * ) Notice: Subject to any disclaimer, the term of this patent is extended or adjusted under 35 U.S.C. 154(b) by 0 days.

(21) Appl. No.: 09/807,097

(22) PCT Filed: Oct. 8, 1999

(86) PCT No.: PCT/US99/23524

§ 371 (c)(1),
(2), (4) Date: Apr. 6, 2001

(87) PCT Pub. No.: WO00/19894

PCT Pub. Date: Apr. 13, 2000

Related U.S. Application Data
(60) Provisional application No. 60/103,506, filed on Oct. 8, 1998.

(51) Int. Cl.⁷ .................................................. A61B 5/05

(52) U.S. Cl. ...................... 600/547; 600/426; 600/407; 600/373; 600/591; 606/34; 607/901

(58) Field of Search ................................ 600/426, 407, 600/591, 373, 393, 547; 606/34; 607/901

(56) References Cited

U.S. PATENT DOCUMENTS

| | | | | |
|---|---|---|---|---|
| 5,630,426 A | * | 5/1997 | Eggers et al. | 128/734 |
| 5,800,350 A | * | 9/1998 | Coppleson et al. | 600/372 |
| 6,026,323 A | * | 2/2000 | Skladnev et al. | 600/547 |

* cited by examiner

Primary Examiner—Shawntina Fuqua
(74) Attorney, Agent, or Firm—Gottlieb, Rackman & Reisman, P.C.

(57) ABSTRACT

A method and apparatus for recognizing tissue types measures at least two separate and distinct properties of a tissue specimen using a probe tip containing electrodes coupled to circuitry that applies a measuring current and obtains values of electrical properties of the tissue such as conductivity and potential difference. An algorithm then uses the values to determine the tissue's type and condition.

12 Claims, 5 Drawing Sheets

APPARATUS FOR RECOGNIZING TISSUE TYPES

This application claims the benefit of provisional application 60/103,506 filed Oct. 8, 1999.

FIELD OF THE INVENTION

This invention relates to the field of tissue type recognition on human subjects and more particularly to the field of tissue recognition by performing electrical measurements of tissue surfaces, e.g. the cervix.

BACKGROUND OF THE INVENTION

The medical profession often needs to have an objective assessment of the health of the tissue of a patient. The patient may have suffered tissue damage as a result of malignancy, accidental or deliberate trauma such as damage incurred during a surgical operation. Tissue damage may also result from some other more persistent irritation such as being confined to bed which can lead to bed sores. It is valuable for a medical practitioner to be able to tell in advance the condition of certain tissue so he can determine the type of treatment that would benefit the patient.

It is common practice to measure an electrical property of tissue using a probe to determine its type and health. Different types of tissue have different electrical resistances. For example, malignant tumors have lower electrical resistance than healthy tissue.

Current methods of electrical tissue recognition, however, employ only one type of electrical measurement to characterize the tissue under examination, generally leading to ambiguous diagnoses of the tissue type. These measurements have included the conductivity or impedance at various frequencies using two, three and four terminals. A variety of electrode types and spacings have been employed to achieve control over the depth of penetration of the measuring current. Ollmar in U.S. Pat. No. 5,353,802 claims to have been able to control the depth of the measurement with three electrodes.

As early as 1918 Clowes (J. Proc. Soc. Exp. Biol. Med., 15, 107 (1918))showed that malignant tumors have lower electrical resistance than does healthy tissue. Schwan (Adv. Biol. Med. Phys., 5, 147–209,1957)and Webster (Ed. Electrical Impedance Tomography, Bristol, England, Adam Hilger 1990) have published extensively on the subject of tissue impedance measurement.

Machida et al in U.S. Pat. No. 4,537,203 have described an abnormal cell detecting device which employs multiple electrodes and two frequencies. The electrical property measured in this case is conductivity only. By making a number of measurements over a breast they claim to be able to detect the presence of a cancerous lesion within the breast. Ratios of conductivities are calculated and are displayed as a two dimensional array for interpretation by the operator. Machida employs the determination of only one electrical property, conductivity.

Vrana et al in U.S. Pat. No. 4,038,975 have described a circuit for measuring the electrical impedance of tissue in terms of its real and imaginary terms. From these figures they diagnose the presence of abnormalities in the tissue. They employ only one method of stimulation to make the measurement.

Juncosa et al in U.S. Pat. No. 4,729,385 have detailed an electrode suitable for the determination of the electrical impedance of cavity walls in, for example, blood vessels.

Following on the pioneering work of Langman and Burr (Amer. J. Obst. Gynec., 57, 274 (1949)) potential differences have been suggested as a means to detect skin cancer by Melczer and Kiss (Nature 179, 1177 (1957)) and by other investigators. Potential differences have been used by Faupel et al in U.S. Pat. Nos. 4,955,383, 5,217,014, 5,320,101 etc. to detect areas of neoplasm in the breast. That inventor uses multiple electrodes but again detects only one electrical property, potential differences. Melczer has published extensively on this subject and on skin resistance measurements for the detection of abnormalities.

Potential difference measurements are commonly used for both heart and brain function monitoring. Cudahy et al in U.S. Pat. No. 5,184,620 have proposed the use of multiple electrodes for signal detection and injection which are automatically selected for optimal effectiveness on the basis of the measured signals.

Honma et al in U.S. Pat. No. 4,966,158 have patented a switched electrode system for skin moisture measurement based on low frequency electrical conductivity.

Eggers et al in U.S. Pat. No. 5,630,426 have proposed using two electrodes on a probe, one of which detects the presence of an abnormality and the second applies energy to treat the abnormality. Only one form of electrical detection is used to arrive at the decision to treat the area being examined.

Electrical tomography has also been proposed by Brown et al in U.S. Pat. Nos. 4,617,939, 5,184,624 etc. for the delineation of objects within a subject. These devices use a multiplicity of electrodes to map out the conductivity patterns within the tissue of the subject. Once again only conductivity is measured.

The dielectric constant of breast tumor tissue was shown by Fricke and Morse (J. Cancer Res., 10, 340–376, 1926) to be distinctly different to that of normal breast tissue. These measurements have to be done in vitro so are not relevant to the detection of abnormalities during patient screening.

Frei et al in U.S. Pat. No. 4,291,708 describe an apparatus for the detection of breast cancer in vivo by measuring the dielectric properties of the breast using a plurality of electrodes positioned above and below the breast. Bridges in U.S. Pat. No. 5,704,355 has proposed an improvement on this concept by focusing the applied electromagnetic energy into a small area which is scanned over the breast.

Sets of four microelectrodes have been used by Kottra and Fromter (European Journal of Physiology 402: 409–420, 1984) to record the resistance across and between cells by measuring electrical impedance of cell monolayers.

Thus, it is desirable to have a system that employs more than one form of electrical property determination on the same area of tissue for a more accurate diagnosis of tissue type and condition.

SUMMARY OF THE INVENTION

The present invention provides an accurate tissue type method and apparatus. The method comprises measurements of at least two separate and distinct electrical properties of a tissue specimen. The apparatus comprises a probe having a handle connected to a shaft with a tip at its end. The tip contains a number of electrodes electrically coupled to tissue recognizing circuitry located either in the handle or a console and connected to the tip via a cable. The circuitry applies a measuring current to the tissue via the electrodes to obtain the values of particular electrical properties of the tissue, such as conductivity and potential difference. An algorithm is applied to the obtained values to determine the tissue's type and condition.

Thus, by combining a number of electrical properties and measurement methods in such a manner that they complement each other and thereby remove the ambiguity of any one measurement on its own, the present invention provides a more accurate method and apparatus for tissue type recognition.

The particular measurements of tissue electrical properties that are the subject of this invention comprise two or more of the following:

1. Three electrode measurements as described below, i.e pulse and decay (method 1).

2. Two electrode conductivity and phase measurements at frequencies between 1 Hz and 10 MHz 3. Three electrode measurements where a large reference electrode is employed and separate current delivery and voltage sensing electrodes are used to make conductivity and phase angle measurements at frequencies between 1 Hz and 10 MHz 4. Four electrode measurements where a pair of electrodes are used to apply current and a second pair are used to measure the voltage drop induced in the tissue which provides data on the conductivity and phase angle characteristics at frequencies between 1 Hz and 10 MHz.

5. Measuring systems that employ electrodes whose spacing ranges from ten times the electrode size to one tenth of the electrode size whilst making the above measurements. The electrode perimeter may be from 1 micrometer to 100 millimeters.

6. Dielectric constant measurement on the tissue.

7. Induced polarization measurements employing a current carrying coil with or without electrodes attached to the tissue.

8. Measurement of the potential difference between the tissue that is to be diagnosed and other tissue sites on the patient.

BRIEF DESCRIPTION OF THE DRAWINGS

A better understanding may be obtained from the following description in conjunction with the figures in which:

FIG. 1b is an enlarged view of the probe's tip from FIG. 1a;

FIG. 4 is an illustration of a probe tip with electrodes of unequal size; and, FIG. 5 is a block diagram of an exemplary tissue recognizing circuitry for probes with four electrodes, such as those in FIGS. 1a & 2a.

DETAILED DESCRIPTION

Figure 1A:
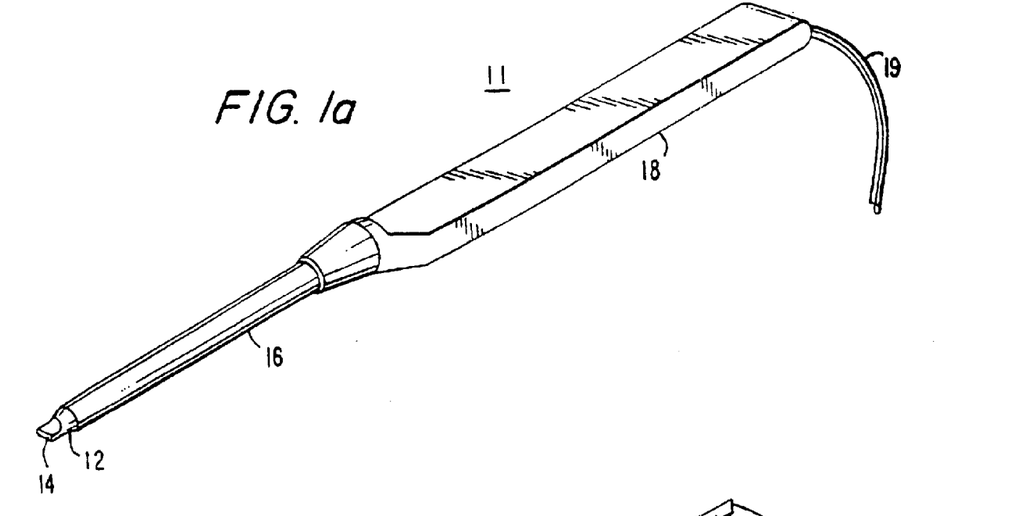
FIG. 1a is an illustration of a probe fitted with four electrodes at the tip.
Figure 1B:
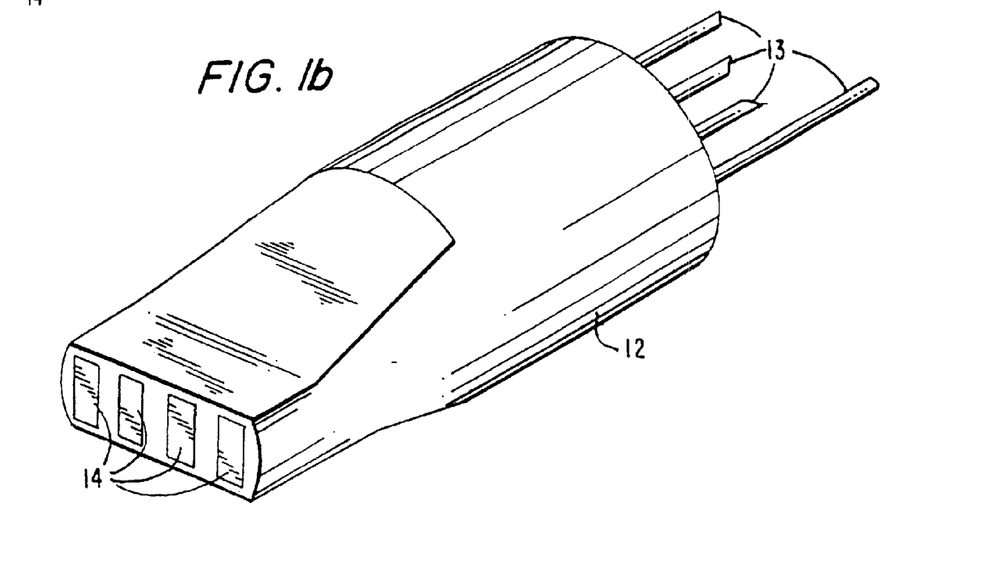

Referring to FIG. 1a, there is shown an exemplary tissue-type recognizing probe 11 in accordance with the principles of the present invention. A tip 12 is coupled to a handle 18 via a shaft 16. The tip 12 has a number of electrodes 14 at its front to establish electrical contact with a tissue specimen (not shown). FIG. 1b details the electrodes 14 at the front of the tip 12. Electrodes 14 at the front of the tip 12 are connected by wires 13 to control circuitry which may be in the handle 18 of FIG. 1a or in a separate console connected via a cable 19. The electrodes 14 can be used in pairs to measure the pulse response of the tissue as described below or as a group of four to perform four terminal conductivity measurements. Their type and position may be changed to control the penetrating depth of the measuring current.

The effectiveness of the electrode 14 contact on a tissue specimen can be checked by making measurements on the three adjacent pairs of the electrodes which should yield similar figures when they are touching the same tissue types if the contact is good. In the event that the figures differ the data would probably be discarded because of the possibility of error due to uncertainty about the type of tissue being measured or the quality of contact.

The magnitude of the current injected into the patient must be limited for safety reasons. The accepted figure for low frequency current injected by electrodes where the current cannot pass via the heart is 100 microamps between 0.1 Hz and 1 kHz. This can be multiplied by the frequency in kilohertz up to a maximum multiplier of 100, i.e. the current can be up to 10 milliamps at 100 kHz and above. The voltages and currents employed for these measurements must be moderated in accordance with these safety requirements. High figures are typically chosen to maintain the signal to noise ratio at an adequate level.

The particular electrical property measurement methods used in the present invention comprise two or more of the following:

1. Three electrode measurements as described below, i.e. pulse and decay (method 1).

2. Two electrode conductivity and phase measurements at frequencies between 1 Hz and 10 MHz 3. Three electrode measurements where a large reference electrode is employed and separate current delivery and voltage sensing electrodes are used to make conductivity and phase angle measurements at frequencies between 1 Hz and 10 MHz.

4. Four electrode measurements where a pair of electrodes are used to apply current and a second pair are used to measure the voltage drop induced in the tissue which provides data on the conductivity and phase angle characteristics at frequencies between 1 Hz and 10 MHz.

5. Measuring systems that employ electrodes whose spacing ranges from ten times the electrode size to one tenth of the electrode size whilst making the above measurements. The electrode perimeter may be from 1 micrometer to 100 millimeters.

6. Dielectric constant measurement on the tissue.

7. Induced polarisation measurements employing a current carrying coil with or without electrodes attached to the tissue.

8. Measurement of the potential difference between the tissue that is to be diagnosed and other tissue sites on the patient.

The three electrode measurement method is done as follows: three electrodes can be selected to be anodes, cathodes or high impedance (no connection) under the control of a microprocessor. A voltage of 1.25 volts is applied to the electrodes to charge the tissue. After a short period of time (250 $\mu$s) the voltage source is disconnected and a voltage supplied for charging the tissue. This supply has suitable over-voltage and over-current protection for the safety of the patient. Electrical contact is made between the electrodes and tissue by the presence of an electrolyte. This may be a naturally occurring mucus covering the tissue or an artificially applied conductive fluid or gel. The electrical measurements are stimulated by the delivery of 1.25 volt electrical pulses of 250 $\mu$s duration. Following removal of the applied electrical potential, the residual charge dissipates within the tissue with a decay constant dependent on tissue capacitance, the electrode/tissue interface and electronic and ionic conductance. This "relaxation curve" is characteristic of the underlying tissue type. The shape of the electrical relaxation curve is also highly dependent on hardware-specific features including the electrode material composition, surface composition and position. The measured tissue response is filtered, digitized at 9 $\mu$s intervals, and thereafter processed in a probe console.

The electrical pulses are delivered across varying combinations of the three electrodes. In each case, one electrode is active while the remaining two act as a reference. Electrical pulse delivery and the corresponding relaxation curve measurements are continually cycled through the three possible electrode combinations. This feature allows the detection of conditions which result in an asymmetrical charge imbalance between electrodes, such as partial contact. In addition, electrode cycling minimizes electrochemical degradation. Each tissue observation incorporates several relaxation curves recorded for each of the three electrode configurations. After each series of measurements an electrode discharge cycle is implemented.

A typical three electrode measurement cycle is divided into intervals. During the first ("calibration") interval an internal calibration of the instrument takes place. The calibration is carried out under microprocessor control. This method is a successive approximation type of search which reduces the calibration time from $2^n$ iterations to n+1 iterations.

During three ("current measurement") intervals (4–10.5 ms; 18.5–25 ms; 32.5–39 ms), a current (the inrush current) is injected respectively from one of the three possible probe tip electrode configurations (in which one electrode is at anode potential and two are cathodes).

A probe orientation interval (47–48.5 ms) follows, during which the proper orientation of the probe against the tissue surface is checked.

This if followed by a discharge interval (48.5–71.5 ms), in which the surface under examination is discharged, a data analysis algorithm is executed, and the user interface is updated. During each of the three current measurement intervals four square current pulses of approximately 250 $\mu$s duration are employed, separated by 1.8 ms. Three measurements are made of the decay amplitude of each of the first and fourth current pulses during the time prior to the second pulse or prior to the end of the current measurement interval. A series of 18 electrical measurements of pulse decay are made in each 71.43 $\mu$s cycle. A set of parameters is generated to parametrize the shape of the inrush current and voltage decay curves in each interval such as with a multiple exponential best fit.

Alternative shape parameterizations include transforming the data with ordinate and abscissa operators such that they become piecewise straight line segments. Such operators include taking logs so as to produce log/log displays, using inverse time as the abscissa or any other transformations that provide good fit to the data. Parameters associated with the transformed functions can then be associated with the degree of tissue abnormality. Typical operations that can be applied to the curves and variables that can be extracted for use as discriminants are as follows:

1. The slope and intercept of the log voltage/inverse time plot of the curves.
2. The slope and intercept of the long voltage/log time plot of the curves.
3. The subtraction, addition, multiplication or division of or by a function to diminish the a priori known obscuration effect of some artifact of, or noise source within the system.
4. The slope of the voltage vs. current curve at the start of the relaxation curve.
5. The relationship between the parameters of the inrush current curve and the parameters of the relaxation curve.
6. The use of integrals of segments of the curves based on time intervals.
7. The use of integrals of segments of the curves based on voltage intervals.
8. The use of integrals of segments of the curves based on current intervals.
9. The magnitudes of the offsets.

Tissue classification parameters are extracted from the digitized electrical data, in addition to various parameters extracted for the detection of poor contact conditions. Some of the electrical parameters are functions derived from various portions of the measured relaxation curves. These parameters are then passed to a processor chip for classification.

Thus the apparatus of the present invention categorizes biological tissue by having a probe tip able to select a tissue surface area by contact and applying a group of sequential current pulses from the probe tip to each of a succession of selected tissue surface areas. The sequential pulses occur within groups that occur at a rate fast enough so that they are applied to substantially the same tissue surface area. A circuit then derives values for a group of parameters that indicate the response to the group of sequential current pulses applied to each selected tissue surface area. A memory stores a catalog of tissue types that are associated with respective subsets of groups of parameter values. The processor then compares the group of parameter values that indicate the response of the selected tissue surface area with the stored subsets of groups of parameter values to categorize the tissue surface area.

The parameters in the parameter group are not necessarily associated on a one-to-one basis with the sequential current pulses in the current pulse group. The successive groups of sequential current pulses may be separated in time from each other by a time interval substantially greater than the time interval between the sequential current pulses within an individual group.

During any current pulse for which a tissue response is desired multiple measurements of the tissue-potential are taken during decay of the potential following application of the current pulse. Furthermore, the system permits at least two parameter values to be derived during the potential decay following each current pulse for which a tissue response is desired thereby allowing a more sophisticated parameterization of the current decay than a simple exponential. Enough measurements are made during the current decay so that each of the parameters may be derived from several of the multiple measurements taken during the decay of the current pulse for which a tissue response is desired. These multiple parameters are then available so that the processor can categorize any tissue surface in accordance with at least two parameter values derived during the potential decay following each of at least two current pulses. In general these two current pulses are separated by at least one other current pulse which is not used by the processor to categorize the tissue.

To aid in the complete discharge, during the discharge interval the three electrical probe tip elements are made active cathodes and kept at low impedance. This is quite contrary to the normal construction of measuring electrodes where the impedance is kept high so that the current characteristics of the object being measured are effectively isolated from the current flow in the measuring instrument. Essentially the benefit of isolation is traded off for the rapidity of recovery of the tissue for the next measurement cycle.

The data obtained from measuring an unknown region of tissue is compared with data obtained from measuring known tissue types using the same apparatus. From this comparison, a diagnosis of the tissue type and its health can be estimated. If the data for different known tissue types is not easy to separate, a statistical technique such as discriminant analysis may be used. Discriminant analysis is explained in *Discrimination and Classification* by D. J. Hand (New York: John Wiley & Sons Inc, 1981). This process defines a set of measurements that correspond to each known tissue type.

One of the many tissue types detectable by the present invention is cancer and precancer. By measuring two electrical properties it is often possible to differentiate tissue types into those that are normal and those that are showing neoplastic abnormalities. Prior art methods of measuring a single electrical property leads to ambiguous indications that may well be indicative of the presence of abnormal tissue but because of the high level of false positive indications are not useful for patient screening.

The present invention finds particular application in the investigation of confined spaces such as the walls of arteries, veins, canals, the digestive tract, the urinary tract, etc. It has the advantage over other methods of tissue typing in that the detection head is intrinsically small and needs only wires to activate it.

Pressure sores are also detectable on those confined to wheel chairs or beds. Left undetected, such pressure sores result in major lesions which require lengthy and costly treatment. Measurement of the electrical properties of the tissue can detect the loss of adequate blood flow to particular areas and thereby warn of the onset of a lesion. The prior art method of measuring a single electrical property does not provide a warning of sufficient reliability to be useful in screening. By combining two or more properties we have found that the early onset of tissue deterioration caused by restricted blood supply can be detected.

Skin cancers of various types have been claimed to be detectable by electrical measurements but the proposed methods set out in the prior art have not been shown to be sufficiently reliable to be used for screening patients. This invention over comes the limitations of previous methods. For example, Basal cell carcinoma is a commonly occurring skin cancer that is amenable to detection by the methods described in this patent.

To further illustrate the present invention's utility, consider the case of the cervix where it is desirable to detect cervical intraepithelial neoplasia, CIN. There are basically three tissue types present on the cervix. They are squamous, columnar and CIN. There are many other minor types also present such as tissues that are in transition from one type to another. For the purposes of this explanation it is sufficient to limit the discussion to the three basic types. Both columnar and CIN tissues tend to be highly vascularised and to have high electrical conductivity. Squamous tissue is composed of relatively mature, flat cells that give it a low conductivity. These groups of tissue types can therefore be readily separated by their electrical conductivity alone. This separation is not clinically useful, however, because columnar tissue occurs frequently on the cervix and is quite healthy. Its conductivity is similar to that of CIN tissue.

To complement the above separation by electrical conductivity, and to thereby achieve an accurate diagnosis, another electrical property of the tissues needs to be measured to separate columnar from CIN tissue. We have found that the use of the pulse and decay method will differentiate between columnar tissue and CIN. (Method 1) A voltage pulse of amplitude between 0.1 and 2 volts is applied across one pair of the electrodes shown in FIG. 1 for a period of 10 to 1000 microseconds. The voltage supply is then disconnected and the voltage appearing across the electrodes is logged as it decays away. The shape of this decay curve is indicative of the tissue type and its health. To speed the decay a resistor may be fitted in place across the pair of electrodes.

The shape of the decay curve provides sufficient reliability and the needed differentiation of columnar from CIN and cancer types. By combining the two measures of electrical properties of the cervical tissue, the presence of abnormal tissue in the form of cancerous or precancerous tissue types can be detected in the presence of normal tissue types.

Furthermore this diagnosis can be performed in situations where it would be difficult if not impossible to measure the optical properties of the tissue to aid diagnosis.

Figure 2A:
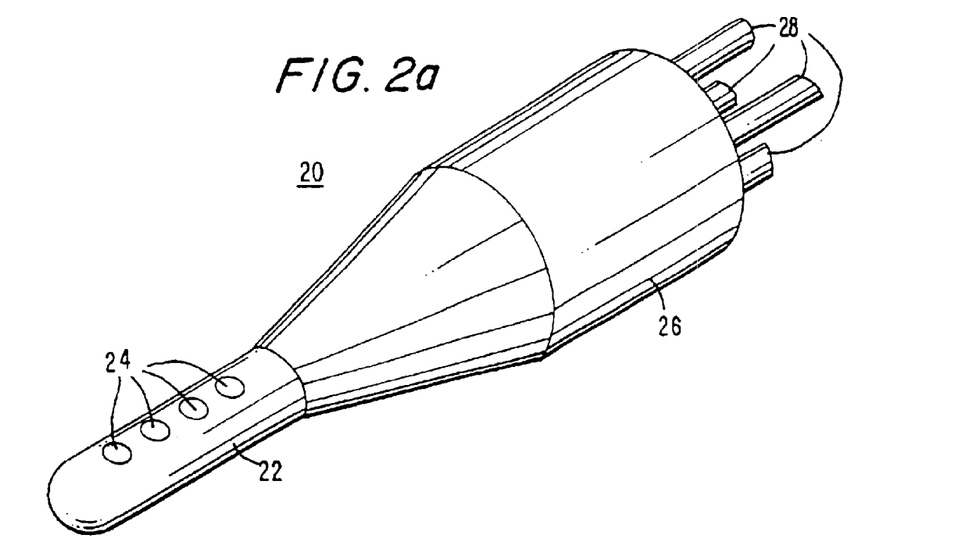
FIGS. 2a, 2b and 2c are illustrations of probes intended for performing examinations of the walls of narrow canals.
Figure 2B:
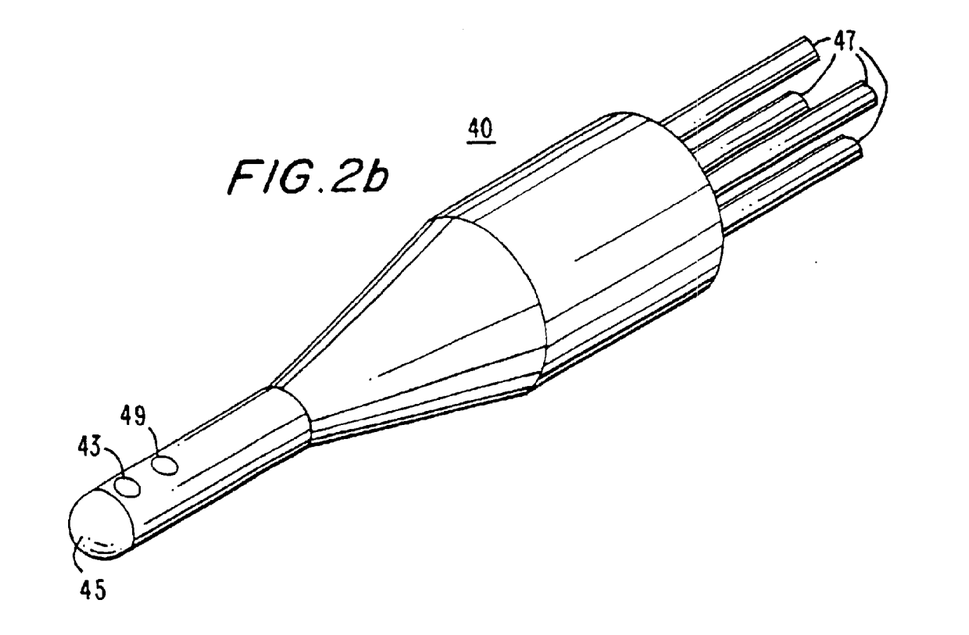
Figure 2C:
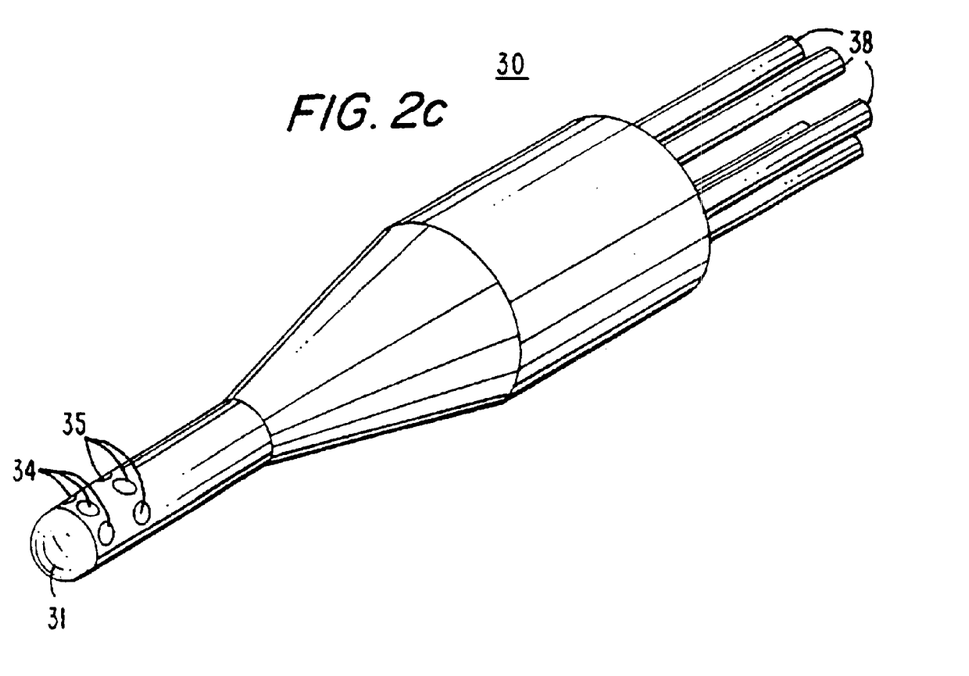

FIGS. 2a, 2b and 2c show probe tips 20, 40 and 30, respectively, designed for measurements in narrow canals. The tips 20, 40 and 30 attach to a probe shaft similar to the shaft 18 of FIG. 1a and in the same manner as tip 12 in FIG. 1b. Referring back to 2a, the electrodes 24 on the tip 22 of the probe 20 are connected by wires 29 to tissue recognizing circuitry.

FIG. 2b shows a probe tip 40 with a different electrode configuration where two of the electrodes 24 of FIG. 2a are combined into a common large electrode 45 at the front of the probe tip 40. Two other electrodes 43 and 49 make up the complete system. When the probe is being used to measure tissue conductivity, current is fed between electrodes 49 and 45 and the voltage drop is measured between 43 and 45. When making pulse and decay determinations, (method 1) electrodes 43 and 49 or 43 and 45 are employed. This configuration has the advantage of needing fewer electrodes and the measuring zone is closer to the tip of the probe.

FIG. 2c illustrates a probe tip 30 into which are fitted rows of electrodes 34 and 35, typically eight in each row. In operation the electrodes are used in the same manner described above with respect to the probe 40 in FIG. 2b with electrode 31 as the common electrode and each column of other electrodes being employed in turn. This configuration enables the inside of the canal to be scanned circumferentially without moving the probe. The electrodes 34 and 35 are employed in turn by the electronic circuits so that they select appropriate pairs of electrodes to be energized. This provides a means for scanning electronically rather than mechanically.

This instrument can be applied to the diagnosis and detection of abnormal tissue types in many, otherwise intractable situations such as in the digestive tract where the presence of food undergoing processing would render optical measurements unreliable.

Figure 3:
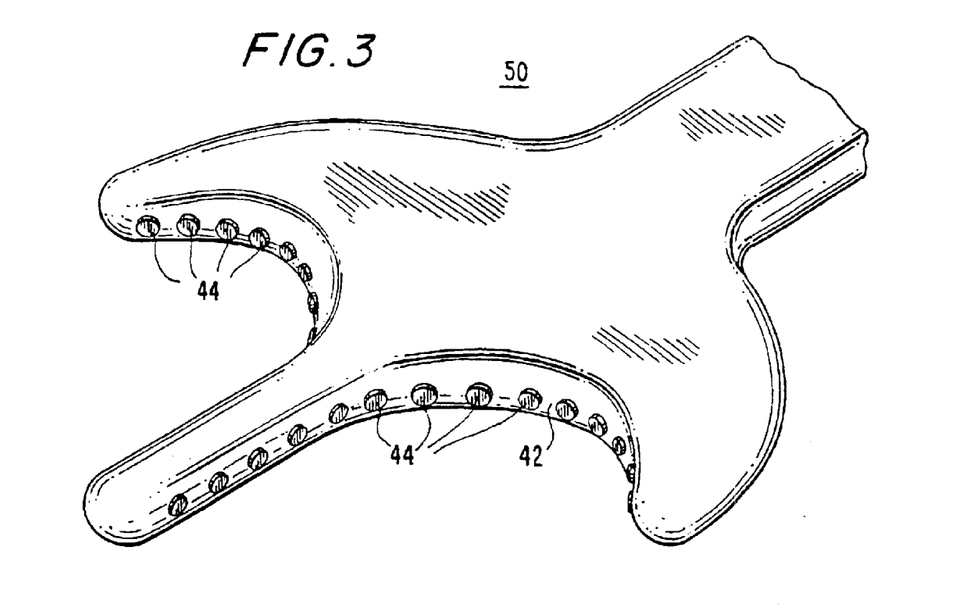
FIG. 3 is an illustration of a probe intended for the examination of a cervix.

Now referring to FIG. 3, there is shown a "wood drill" probe tip 50 for scanning a cervix as described in our U.S. Pat. No 5,800,350 . . . . The curved inner surface 42 of the probe tip 50 is fitted with a number of electrodes 44 which are employed in pairs or in groups to perform the needed electrical property determinations. This configuration allows the scanning of the cervix to be performed by a simple insertion of the tip into the endocervical canal and rotation of the probe to sweep the electrodes over the surface of the cervix.

Figure 4:
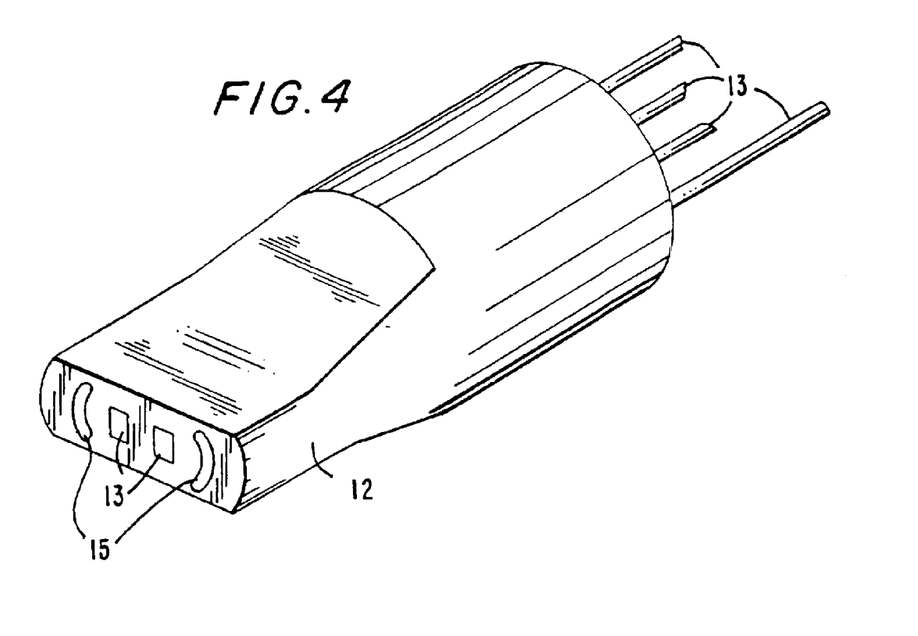

FIG. 4 shows a variant in which the outer pair of electrodes 15 are enlarged with respect to the inner pair 13. This technique improves the homogeneity of the electrical field seen by the inner pair of electrodes 13 when the outer pair 15 are stimulated.

Figure 5:
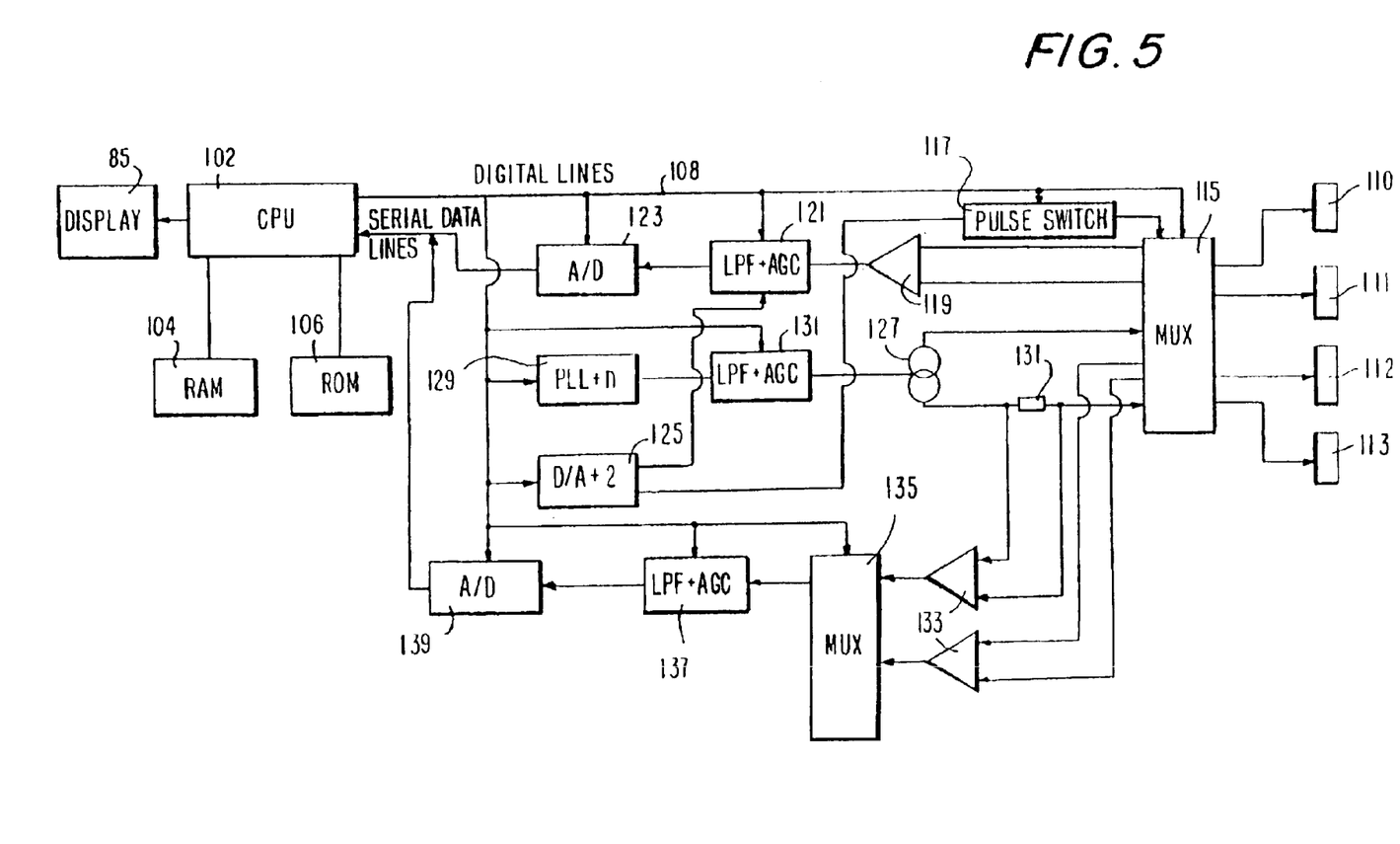

A block diagram of the type of electrical circuit 100 that can be used to make the relevant measurements using these probes is shown in FIG. 5. The system is controlled by a CPU 102 which employs RAM 104 to provide its memory needs and ROM 106 to store the control software. The digital lines 108 carry the commands from the CPU to the many devices that make up the system.

The four electrodes of a probe of the type illustrated in FIG. 1 are shown as 110,111,112, and 113. These are cabled to the two channel multiplexer 115 which controls the manner in which the electrodes are connected. Two types of connection will be described which make it possible to measure four electrical properties of the tissue, viz. the pulse response, the resistance, the reactance, which is related to the dielectric constant of the tissue, and potential differences between parts of the tissue.

At the start of a measuring cycle the multiplexer 115 connects electrodes 111 and 112 to the pulse switch 117. A pulse, typically of length 300 microseconds and amplitude one volt is applied to electrode 111 whilst electrode 112 is grounded. The instrumentation amplifier 119 is also connected to these two electrodes and feeds the voltage signal via the low pass filter and programmable gain amplifier 121 to the analog to digital converter 123. The output of the converter 123 goes to the CPU 102 via the serial data lines 125. The data is logged and analysed for use in the algorithm which will derive a diagnosis of the tissue type. The gain and offset of the amplifier within 121 are controlled by signals from the digital to analog converter 125.

After completing the pulse and decay measurements that employed the circuit described above, electrodes 110 and 113 are connected by the second channel of multiplexer 115 to the programmed alternating current generator 127. The magnitude and frequency of the current fed to the electrodes is controlled by signals originating from the phase locked loop 129 which are fed via the low pass filter and programmable gain amplifier 131 to the voltage controlled current generator 127. The phase locked loop 127 is controlled by the CPU by signals from the digital lines 108. The gain of unit 131 is controlled by digital signals from the lines 108. A resistor 131 inserted in the line to electrode 113 detects the current flowing as a voltage drop.

Electrodes 111 and 112 are connected by multiplexer 115 to the instrumentation amplifier 133 and thence to the multiplexer 135 which sends the signals via the low pass filter and programmable gain amplifier 137 and analog to digital converter 139 to the CPU 102. The voltage drop across resistor 131 is handled in the same manner. These signals are analysed and logged for use as discriminants by the algorithm to reach a tissue diagnosis.

The phase angle of the voltage across resistor 131 is compared with the phase angle of the alternating voltage appearing across electrodes 110 and 113 to yield data on the reactive part of the tissue impedance. The reactive part is a function of the dielectric constant of the tissue so is used as a discriminant by the algorithm during its diagnosis of the tissue.

By discontinuing the feed current to electrodes 110 and 113 from the generator 127 and by raising the gain of the programmable gain amplifier 137 it is possible to measure the DC potential difference that exists between the tissue under electrode 111 and that under electrode 112. This measurement, which is of the order of millivolts can then be employed as a discriminant by the algorithm for tissue diagnosis.

The decision of the algorithm as to the tissue type is fed to the display device 85. This may take many forms. It could be a computer screen, a set of indicator lights that signal the operator, a printer or another computer.

The above description is by way of example to illustrate the type of multiple electrical measurement system that may be employed to embody this invention. It will be appreciated that many other circuits could be employed to measure electrical properties of the tissue.

What is claimed is:

1. A tissue type recognition system for determining a type of unknown tissue, comprising:
   a tip;
   a shaft for coupling said tip to a handle;a plurality of electrodes in said tip;
   tissue recognizing circuitry electrically coupled to said plurality of electrodes;
   wherein said circuitry injects electrical current into said tissue via said electrodes for measuring at least two unique electrical properties of said tissue; and,
   each of said electrical properties is compared with corresponding electrical properties of known tissue types to determine said type of unknown tissue
   wherein said electrodes are configured with an outer pair and an inner pair, said outer pair being larger than said inner pair so that a homogeneity of an electrical field seen by said inner pair is thereby improved.

2. The tissue type recognition system of claim 1 wherein said electrodes are used in pairs to measure a pulse response of said tissue.

3. The tissue type recognition system of claim 1 wherein each of said plurality of electrodes are used to perform a terminal conductivity measurement.

4. The tissue type recognition system of claim 1 wherein contact between said electrodes and said tissue is checked by making measurements on adjacent pairs of said plurality of electrodes.

5. The tissue type recognition system of claim 1 wherein said current is between 0 and 10 milliamps applied at a frequency of at least 100 kHz.

6. The tissue type recognition system of claim 1 wherein the tip further comprises a large electrode.

7. The tissue type recognition system of claim 1 wherein said electrodes are arranged in a number of rows.

8. A method for detecting the presence of abnormal tissue in a cervix, comprising a step for scanning a canal wall electronically by employing in turn electrodes arranged in a number of rows so that appropriate pairs of electrodes are energized thereby simulating movement of one pair of electrodes in a circular scanning motion along said canal wall.

9. A tissue type recognition system for determining a type of unknown tissue, comprising:
   a tip;
   a shaft for coupling said tip to a handle;
   a plurality of electrodes in said tip;
   tissue recognizing circuitry electrically coupled to said plurality of electrodes;
   wherein said circuitry injects electrical current into said tissue via said electrodes for measuring at least two unique electrical properties of said tissue; and,
   each of said electrical properties is compared with corresponding electrical properties of known tissue types to determine said type of unknown tissue wherein the tissue recognizing circuitry further comprises means for measuring a pulse response of said tissue, an electrical resistance of said tissue, a reactance of said tissue, and a potential difference of said tissue.

10. The method for detecting the presence of abnormal tissue in a cervix by conducting a discriminant analysis, said analysis comprising the steps of:
    measuring an electrical conductivity of cervical tissue in said cervix via a first pair of electrodes;
    measuring a pulse and decay property of said cervical tissue in said cervix via a second pair of electrodes; and,
    determining from said conductivity measurement and said pulse and decay properties measurement whether the cervix has normal and abnormal cervical tissue,
    wherein, the step of measuring a pulse and decay property includes measuring a pulse response of the tissue by applying a pulse across said second pair of electrodes and, further, measuring a decay of said pulse across said second pair of electrodes.

11. A method for detecting the presence of abnormal tissue in a cervix by conducting a discriminant analysis according to claim 10, said analysis further comprising the step of determining a reactance of said tissue by:
- measuring a first phase angle of voltage across said tissue
- selecting circuitry electrically coupled to said tissue via a pair of said electrodes;
- measuring a second phase angle of voltage across said pair of electrodes;
- comparing said first and said second phase angles to yield data on the reactive part of the tissue impedance.

12. The method for detecting the presence of abnormal tissue in a cervix by conducting a discriminant analysis according to claim 10, said analysis further comprising the step of measuring a potential difference of said tissue by:
- injecting current into said tissue via a pair of said electrodes;
- discontinuing said current; and,
- raising a gain of a programmable gain amplifier connected to said pair of electrodes.

* * * * *